US012590968B2

(12) United States Patent
Albertson et al.

(10) Patent No.: US 12,590,968 B2
(45) Date of Patent: Mar. 31, 2026

(54) DETECTION AND TREATMENT OF CD30+ CANCERS

(71) Applicant: SEAGEN INC., Bothell, WA (US)

(72) Inventors: Tina Albertson, Bothell, WA (US); Maria L. Smith, Bothell, WA (US)

(73) Assignee: SEAGEN INC., Bothell, WA (US)

(*) Notice: Subject to any disclaimer, the term of this patent is extended or adjusted under 35 U.S.C. 154(b) by 861 days.

(21) Appl. No.: 17/747,591

(22) Filed: May 18, 2022

(65) Prior Publication Data

US 2022/0373553 A1 Nov. 24, 2022

Related U.S. Application Data

(60) Continuation of application No. 16/571,035, filed on Sep. 13, 2019, now Pat. No. 11,366,118, which is a division of application No. 14/376,957, filed as application No. PCT/US2013/025392 on Feb. 8, 2013, now Pat. No. 10,444,241.

(60) Provisional application No. 61/597,547, filed on Feb. 10, 2012.

(51) Int. Cl.

| | |
|---|---|
| ***A61K 39/00*** | (2006.01) |
| ***A61K 47/68*** | (2017.01) |
| ***C07K 16/28*** | (2006.01) |
| ***G01N 33/574*** | (2006.01) |

(52) U.S. Cl.

CPC ... *G01N 33/57492* (2013.01); *A61K 47/6849* (2017.08); *C07K 16/2878* (2013.01); *G01N 2333/70578* (2013.01)

(58) Field of Classification Search

CPC .. A61K 47/6849; C07K 16/2878; A61P 35/00

See application file for complete search history.

(56) References Cited

U.S. PATENT DOCUMENTS

| | | | |
|---|---|---|---|
| 10,444,241 | B2 | 10/2019 | Albertson et al. |
| 11,366,118 | B2 | 6/2022 | Albertson et al. |
| 2006/0177442 | A1 | 8/2006 | Von Strandmann et al. |
| 2008/0241128 | A1 | 10/2008 | Jeffrey |
| 2008/0300192 | A1 | 12/2008 | Doronina et al. |
| 2008/0305044 | A1 | 12/2008 | McDonagh et al. |
| 2008/0317747 | A1 | 12/2008 | Francisco et al. |
| 2009/0018086 | A1 | 1/2009 | Doronina et al. |
| 2010/0158909 | A1 | 6/2010 | McDonagh et al. |
| 2010/0239571 | A1 | 9/2010 | McDonagh et al. |
| 2010/0322920 | A1 | 12/2010 | Keler et al. |
| 2011/0020343 | A1 | 1/2011 | Senter et al. |
| 2011/0064753 | A1 | 3/2011 | Senter et al. |
| 2011/0268751 | A1 | 11/2011 | Sievers et al. |
| 2012/0014943 | A1 | 1/2012 | Lazar et al. |
| 2020/0110091 | A1 | 4/2020 | Albertson et al. |

FOREIGN PATENT DOCUMENTS

| | | | |
|---|---|---|---|
| CN | 1638800 | | 7/2005 |
| CN | 16338800 | | 7/2005 |
| CN | 16338800 | A | 7/2005 |
| CN | 101056655 | | 10/2007 |
| CN | 101056655 | A | 10/2007 |
| JP | 2005-534281 | A | 11/2005 |
| JP | 2009-511495 | A | 3/2009 |
| WO | WO 2003/059282 | A | 7/2003 |
| WO | WO 2007/044616 | A2 | 4/2007 |
| WO | WO 2008/041594 | A1 | 4/2008 |
| WO | WO 2011/031441 | A1 | 3/2011 |
| WO | WO 2011/109789 | A2 | 9/2011 |
| WO | WO 2013/119990 | A2 | 8/2013 |

OTHER PUBLICATIONS

Sharman et al, ASCO meeting abstract, 30: Spple 3069, May 20, 2012 (Year: 2012).*

Polski et al (Mod Pathol 12:903-6, 1999 (Year: 1999).*

"Phase I Study of HeFi-1 to Treat Cancer With CD30 Protein," ClinicalTrials.gov, retrieved on Jul. 8, 2017 at <http://clinicaltrials.gov/ct2/show/NCT00048880>.

"Seattle Genetics Announces initiation of Phase II Clinical Trial of ADCETRIS(TM) In CD30 Positive Non-Lymphoma Mallgnancies," Seattle Genetics, Investor & News, 2 pages, (2011).

Andreesen et al., "Human Macrophages Can Express the Hodgkin's Cell-Associated Antigen Ki-1 (CD30)," Am J Pathol, 134(1): 187-192, (1989).

Cossu-Rocca et al., "Cytokeratin and CD30 expression in dysgerminoma," Human Pathology, 37:1015-1021, (2006).

Dabbs, "Diagnostic Immunohistochemistry, Theranostic and Genomic Applications," Third Edition, ISBN: 978-1-416u0-5766-6, Copyright 2010, 2006, 2002 by Saunders, an imprint of Elsevier Inc.

EPO Application No. EP 13746038.2, European Examination Report mailed Aug. 23, 2017.

Horie, et al., "CD30: Expression and Function in Health and Disease," Seminars in Immunology, 10(6): 457-470, (1998).

Katz et al. "Brentuximab Vedotin (SGN-35)," Clinical Cancer Research, 17(20):6428-6436, (2011).

Kovtun et al., "Cell killing by antibody-drug conjugates," Cancer. Letters, 255:232-240, (2007).

Mechtersheimer et al., "Expression of Ki-1 Antigen (CD30) in Mesenchymal Tumors," Cancer, 66(8): 1732-1737, (1990).

Mechtersheimer et al., "Expression of Ki-1 Antigen (CD30) in Mesenchymal Tumors," Cancer, 66:1732-1737, (1990).

Pallesen et al., "Ki-1 (CD30) Antigen Is Regularly Expressed by Tumor Cells of Embryonal Carcinoma," Am J Pathol, 133(3):446-450, (1988).

Schwarting et al., "BER-H2: A New Anti-Ki-1 (CD30) Monoclonal Antibody Directed at a Formol-Resistant Epitope," Blood, 74(5): 1678-1689, (1989).

(Continued)

*Primary Examiner* — Lei Yao

(74) *Attorney, Agent, or Firm* — Alston & Bird LLP

(57) ABSTRACT

The application provides methods of diagnosis, prognosis, prophylaxis and treatment of $CD30^+$ cancers.

4 Claims, No Drawings

(56) References Cited

OTHER PUBLICATIONS

Trovato et al., "Expression of CD30 Ligand and CD30 Receptor in Normal Thyroid and Benign and Malignant Thyroid Nodules," Thyroid, 11(7):621-628, (2001).
Wolters Kluwer's Adis R&D Insight, "Brentuximab Vedotin," Drugs RD, 11(1): 85-95, (Mar. 1, 2011).
EPO Application No. EP 13746038.2, Supplementary European Search Report and European Search Opinion, mailed Oct. 5, 2015.
U.S. Appl. No. 14/376,957, Final Office Action mailed Jul. 13, 2017.
U.S. Appl. No. 14/376,957, Final Office Action mailed Aug. 31, 2016.
U.S. Appl. No. 14/376,957, Final Office Action mailed Nov. 6, 2015.
U.S. Appl. No. 14/376,957, Non-Final Office Action mailed Mar. 8, 2017.
U.S. Appl. No. 14/376,957, Non-Final Office Action mailed Mar. 30, 2018.
U.S. Appl. No. 14/376,957, Non-Final Office Action mailed May 12, 2016.
U.S. Appl. No. 14/376,957, Non-Final Office Action mailed Jul. 9, 2015.
U.S. Appl. No. 14/376,957, Notice of Allowance and Examiner Initiated Interview Summary mailed Jun. 14, 2019.
U.S. Appl. No. 14/376,957, Notice of Allowance and Examiner Initiated Interview Summary mailed Sep. 26, 2018. .
U.S. Appl. No. 14/376,957, Requirement for Restriction/Election mailed Mar. 10, 2015.
U.S. Appl. No. 16/571,035, Final Office Action mailed Dec. 21, 2021.
U.S. Appl. No. 16/571,035, Non-Final Office Action mailed Aug. 6, 2021.
U.S. Appl. No. 16/571,035, Notice of Allowance and Interview Summary mailed Feb. 23, 2022.
U.S. Appl. No. 16/571,035, Requirement for Restriction/Election mailed Mar. 8, 2021. .
WIPO Application No. PCT/US2013/1025392, International Preliminary Report on Patentability, issued Oct. 1, 2014.
WIPO Application No. PCT/US2013/1025392, International Search Report, mailed Apr. 24, 2013.
WIPO Application No. PCT/US2013/1025392, Written Opinion of the International Searching Authority, mailed Apr. 24, 2013.

* cited by examiner

DETECTION AND TREATMENT OF CD30+ CANCERS

CROSS-REFERENCE TO RELATED APPLICATIONS

The present application is a continuation of U.S. Ser. No. 16/571,035 filed Sep. 13, 2019, which is a divisional of U.S. Ser. No. 14/376,957 filed Aug. 6, 2014, now U.S. Pat. No. 10,444,241, which is a US national stage of PCT/US2013/025392 filed Feb. 8, 2013, which claims the benefit of U.S. 61/597,547 filed Feb. 10, 2012.

BACKGROUND

CD30 is a 120 kilodalton membrane glycoprotein (Froese et al., 1987, J. Immunol. 139: 2081-87) and a member of the TNF-receptor superfamily. CD30 is a proven marker of malignant cells in Hodgkin lymphoma and anaplastic large cell lymphoma (ALCL). CD30 was originally identified on cultured Hodgkin's-Reed Steinberg (H-RS) cells using the monoclonal antibody Ki-1 (Schwab et al., 1982, Nature 299:65-67).

CD30 has limited expression on normal tissues in humans. This makes CD30 an attractive target for cancer therapies. CD30 expression has been identified, however, on only a small number of cancers. Further, for some cancers, reporting of CD30 expression has been with antibodies that have non-CD30 related cross-reactivity, such as, for example, Novocastra's NCL-L-CD30 antibody, and is not reliable. It would be helpful to identify cancers that express CD30 and that can be treated using CD30-directed therapies. The present invention addresses this and other needs.

BRIEF SUMMARY

The invention provides, inter alia, methods of diagnosis, prognosis, prophylaxis and treatment and monitoring treatment of ovarian cancer (e.g., ovarian serous carcinoma), skin cancer (e.g., melanoma, and skin squamous cell carcinoma), breast cancer (e.g., triple negative breast cancer), thyroid carcinoma (e.g., anaplastic thyroid carcinoma), pancreatic carcinoma (e.g., undifferentiated pancreatic carcinoma), lung cancer (e.g., small cell and squamous cell), anal cancer (e.g., anal squamous cell carcinoma), thymic carcinoma, endometrial carcinoma, and carcinoma of unknown primary. Also provided are methods of diagnosis, prognosis, prophylaxis and treatment and monitoring treatment of genitourinary squamous cell carcinomas, gynecologic carcinosarcomas, urethral squamous cell carcinoma, uterine carcinosarcoma, sertoli cell tumor, leydig cell tumor, and pancreatic adenocarcinoma.

In one aspect, a method of detecting expression of CD30 in a sample of a patient is provided. The sample can be, for example, from the ovary, skin, endometrium, lung, breast, thyroid, pancreas, anus, thymus, or other tumor site (e.g., gynecological cancer tumor site or genitourinary cancer tumor site of the patient). In some embodiments, the sample is a tissue sample. In one aspect, the tissue is fixed. In one aspect, the fixed tissue sample is contacted with an antibody that binds specifically to CD30, and the binding of the antibody to the fixed tissue sample is detected to determine whether CD30 is expressed in the sample. Expression of CD30 on the fixed tissue sample indicates that the patient has a CD30 expressing cancer. In some embodiments, the sample is fixed with formalin and embedded in paraffin.

In another aspect, a method is provided for diagnosing, prognosing, determining a treatment protocol or monitoring treatment of a patient having cancer. In one aspect, the patient has primary or metastatic ovarian cancer (e.g., primary or metastatic ovarian serous carcinoma). In another aspect, the patient has primary or metastatic skin cancer (e.g., primary or metastatic melanoma and/or skin squamous cell carcinoma). In another aspect, the patient has primary or metastatic breast cancer (e.g., primary or metastatic triple negative breast cancer). In another aspect, the patient has primary or metastatic thyroid cancer (e.g., primary or metastatic anaplastic thyroid carcinoma). In another aspect, the patient has primary or metastatic pancreatic cancer (e.g., primary or metastatic undifferentiated pancreatic carcinoma or adenocarcinoma). In another aspect, the patient has primary or metastatic lung cancer (e.g., primary or metastatic small cell or squamous cell lung cancer). In another aspect, the patient has primary or metastatic anal cancer (e.g., primary or metastatic anal squamous cell carcinoma). In another aspect, the patient has primary or metastatic thymus cancer (e.g., primary or metastatic thymic carcinoma). In another aspect, the patient has primary or metastatic endometrial carcinoma. In another aspect, the patient has carcinoma of unknown primary. In another aspect, the patient has primary or metastatic urethral cancer (e.g., urethral squamous cell carcinoma). In another aspect, the patient has primary or metastatic uterine carcinosarcoma. The method includes determining CD30 expression in cells in a tumor sample taken from the patient, wherein the presence of detectable CD30 expression is used in the diagnosis, prognosis, determining a treatment protocol or monitoring treatment of the patient. The sample can be a formalin fixed paraffin embedded sample. The method can further include administering an effective regimen of a CD30-directed therapy (e.g., anti-CD30 antibody or anti-CD30 antibody drug conjugate) to the patient if the determining step indicates a detectable level of CD30. In some aspects, the presence of CD30 expression at a certain level will be used as a cut-off level to determine whether a patient may benefit from treatment with a CD30-directed therapy. For example, in one aspect, a cut-off of 10% is used to classify a patient as one that has a likelihood of benefitting from CD30-directed therapy. Accordingly, in such embodiments, if a tumor sample taken from the patient has at least 10% CD30 positive tumor cells (i.e., at least 10% of the malignant and/or atypical cells in the sample are CD30 positive), the patient is classified as a patient that has a likelihood of benefiting from treatment with CD30-directed therapy. In some embodiments, a tumor sample taken from the patient will have at least 10%, 15%, 20%, 25%, 30%, 35%, 40%, 45%, 50%, 60%, 70%, 75%, 80%, or 85% CD30 positive tumor cells (i.e., at least 10%, 15%, 20%, 25%, 30%, 35%, 40%, 45%, 50%, 60%, 70%, 75%, 80%, or 85% of the malignant and/or atypical cells in the sample are CD30 positive). In preferred embodiments, at least 10%, 15%, 20%, 25%, 30%, 35%, 40%, 45%, 50%, 60%, 70%, 75%, 80%, or 85% of the tumor cells in the sample express CD30 when using an antibody that specifically binds to the extracellular domain of CD30 (e.g., BerH2 antibody) as the detection antibody.

In another aspect, a method is provided for identifying a patient who will respond to treatment with a CD30-directed therapy; a method is provided for identifying a patient who may benefit from treatment with a CD30-directed therapy; and/or a method is provided for predicting responsiveness of patient to CD30-directed therapy wherein the patient has cancer of the ovary, skin, breast, thyroid, pancreas, lung, anus, thymus, endometrium or cancer of unknown primary. The cancer can be a primary cancer or a metastatic cancer. All of these methods include a step of determining CD30 expression in cells in a tumor sample from the patient, wherein the presence of detectable CD30 expression is used to identify the patient as one that may respond to CD30-directed therapy. In some aspects, patients who have higher levels of CD30 expression are identified as those that have a higher likelihood of responding to CD30-directed therapy. For example, if a tumor sample taken from a patient has at least 10%, 15%, 20%, 25%, 30%, 35%, 40%, 45%, 50%, 60%, 70%, 75%, 80%, or 85% CD30+ positive tumor cells (i.e., at least 10%, 15%, 20%, 25%, 30%, 35%, 40%, 45%, 50%, 60%, 70%, 75%, 80%, or 85% of the malignant and/or atypical cells in the sample are CD30 positive), the patient is indicated as having a higher likelihood of responding to CD30-directed therapy. In preferred embodiments, at least 10%, 15%, 20%, 25%, 30%, 35%, 40%, 45%, 50%, 60%, 70%, 75%, 80%, or 85% of the tumor cells in the sample express CD30 when using the BerH2 antibody or another antibody that specifically binds to the extracellular domain of CD30 as the detection antibody. In one aspect, a method of detecting expression of CD30 in a tissue sample of a patient is provided. Depending on the type of cancer, the tissue sample can be, for example, from the ovary, skin, lung, breast, thyroid, pancreas, endometrium, anus, thymus, or other tumor site of the patient. In some embodiments, the tissue is fixed. The fixed tissue sample is contacted with an antibody that binds specifically to CD30, and the binding of the antibody to the fixed tissue sample is detected to determine whether CD30 is expressed in the sample. Expression of CD30 on the fixed tissue sample indicates that the patient has a CD30 expressing cancer. In some embodiments, the sample is fixed with formalin and embedded in paraffin.

In another aspect, a method is provided for identifying a patient as eligible for CD30-directed therapy. The method comprises determining the level of CD30 expression in a tumor sample taken from the patient. In one aspect, the presence of CD30 in the tumor sample is sufficient to indicate that the patient is eligible for CD30-directed therapy. In one aspect, when at least 10% of the malignant or atypical cells in the sample express CD30, the patient is indicated as eligible for CD30-directed therapy. In one aspect, when at least 15% of the malignant or atypical cells in the sample express CD30, the patient is indicated as eligible for CD30-directed therapy. In another aspect, when at least 20% of the malignant or atypical cells in the sample express CD30, the patient is indicated as eligible for CD30-directed therapy. In another aspect, when at least 25% of the malignant or atypical cells in the sample express CD30, the patient is indicated as eligible for CD30-directed therapy. In another aspect, when at least 30% of the malignant or atypical cells in the sample express CD30, the patient is indicated as eligible for CD30-directed therapy. In another aspect, when at least 35% of the malignant or atypical cells in the sample express CD30, the patient is indicated as eligible for CD30-directed therapy. In another aspect, when at least 45% of the malignant or atypical cells in the sample express CD30, the patient is indicated as eligible for CD30-directed therapy. In another aspect, when at least 40% of the malignant or atypical cells in the sample express CD30, the patient is indicated as eligible for CD30-directed therapy. In another aspect, when at least 50% of the malignant or atypical cells in the sample express CD30, the patient is indicated as eligible for CD30-directed therapy. In another aspect, when at least 60% of the malignant or atypical cells in the sample express CD30, the patient is indicated as eligible for CD30-directed therapy. In another aspect, when at least 70% of the malignant or atypical cells in the sample express CD30, the patient is indicated as eligible for CD30-directed therapy. In another aspect, when at least 75% of the malignant or atypical cells in the sample express CD30, the patient is indicated as eligible for CD30-directed therapy. In another aspect, when at least 80% of the malignant or atypical cells in the sample express CD30, the patient is indicated as eligible for CD30-directed therapy. In another aspect, when at least 85% of the malignant or atypical cells in the sample express CD30, the patient is indicated as eligible for CD30-directed therapy. The patient can have any one of primary or metastatic ovarian cancer, skin cancer, breast cancer, thyroid cancer, pancreatic cancer, lung cancer, anal cancer, thymus cancer, endometrial cancer, and carcinoma of unknown primary. In some aspects, the patient can have any one of a primary or metastatic genitourinary squamous cell carcinoma or gynecologic carcinosarcoma. In one aspect, the patent will have a urethral squamous cell carcinoma, uterine carcinosarcoma, sertoli cell tumor, leydig cell tumor, or pancreatic adenocarcinoma. For example, in one aspect, the patient has ovarian primary or metastatic ovarian cancer (e.g., primary or metastatic ovarian serous carcinoma). In another aspect, the patient has primary or metastatic skin cancer (e.g., primary or metastatic melanoma, and skin squamous cell carcinoma). In another aspect, the patient has primary or metastatic breast cancer (e.g., primary or metastatic triple negative breast cancer). In another aspect, the patient has primary or metastatic thyroid cancer (e.g., primary or metastatic anaplastic thyroid carcinoma). In another aspect, the patient has primary or metastatic pancreatic cancer (e.g., primary or metastatic undifferentiated pancreatic carcinoma or adenocarcinoma). In another aspect, the patient has primary or metastatic lung cancer (e.g., primary or metastatic small cell lung cancer or primary or metastatic squamous cell carcinoma. In another aspect, the patient has primary or metastatic anal cancer (e.g., primary or metastatic anal squamous cell carcinoma). In another aspect, the patient has primary or metastatic thymus cancer (e.g., primary or metastatic thymic carcinoma). In another aspect, the patient has primary or metastatic endometrial cancer. In another aspect, the patient has a carcinoma of unknown primary. The method can further comprise the step of treating the patient with a CD30-directed therapy.

In another aspect, a method of treating a CD30 positive cancer is provided. The method includes administering an effective regimen of a CD30-directed therapy to a patient having cancer and having detectable expression of CD30. In some embodiments, the CD30-directed therapy is an antibody or antibody drug conjugate. The antibody may have effector function. The patient may have previously undergone treatment by surgery, radiation and/or chemotherapy with an agent not directed to CD30 without inducing remission of the cancer. The patient may have previously undergone treatment by surgery, radiation and/or chemotherapy but since relapsed. The patient may have been newly diagnosed with cancer. In some embodiments, the antibody is a chimeric, humanized, or human antibody. In one aspect, the patient has ovarian primary or metastatic ovarian cancer (e.g., primary or metastatic ovarian serous carcinoma). In another aspect, the patient has primary or metastatic skin cancer (e.g., primary or metastatic melanoma, or skin squamous cell carcinoma). In another aspect, the patient has primary or metastatic breast cancer (e.g., primary or metastatic triple negative breast cancer). In another aspect, the patient has primary or metastatic thyroid cancer (e.g., primary or metastatic anaplastic thyroid carcinoma). In another aspect, the patient has primary or metastatic pancreatic cancer (e.g., primary or metastatic undifferentiated pancreatic carcinoma or adenocarcinoma). In another aspect, the patient has primary or metastatic lung cancer (e.g., primary or metastatic small cell or squamous cell lung cancer). In another aspect, the patient has primary or metastatic anal cancer (e.g., primary or metastatic anal squamous cell carcinoma). In another aspect, the patient has primary or metastatic thymus cancer (e.g., primary or metastatic thymic carcinoma). In another aspect, the patient has primary or metastatic endometrial cancer. In another aspect, the patient has a carcinoma of unknown primary.

In some preferred embodiments, the assay to determine level of expression is performed on a tissue section and the level of expression is the percentage of malignant and/or atypical cells in the tissue section that are CD30 positive.

Aspects of the invention will best be understood by reference to the following detailed description of the exemplary embodiments, taken in conjunction with the accompanying drawings, figures, and tables.

Definitions

Unless stated otherwise, the following terms and phrases as used herein are intended to have the following meanings.

The term "antibody" refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., CD30), or (b) conservatively substituted derivatives of such immunoglobulin polypeptides or fragments that immunospecifically bind to the antigen (e.g., CD30). Antibodies are generally described in, for example, Harlow & Lane, Antibodies: *A Laboratory Manual* (Cold Spring Harbor Laboratory Press, 1988). Unless otherwise apparent from the context reference to an antibody also includes antibody derivatives or drug conjugates as described in more detail below.

An "antibody derivative" means an antibody, as defined above, that is modified by covalent attachment of a heterologous molecule such as, e.g., by attachment of a heterologous polypeptide, or by glycosylation, deglycosylation, acetylation or phosphorylation not normally associated with the antibody, and the like.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

An "antigen" is an entity to which an antibody specifically binds.

The term "inhibit" or "inhibition of" means to a reduce by a measurable amount, or to prevent entirely.

The term "agent" means an element, compound, or molecular entity, including, e.g., a pharmaceutical, therapeutic, or pharmacologic compound. Agents can be natural or synthetic or a combination thereof. A "therapeutic agent" is an agent that exerts a therapeutic (e.g., beneficial) effect on cancer cells, either alone or in combination with another agent (e.g., a prodrug converting enzyme in combination with a prodrug). Typically, therapeutic agents useful in accordance with the methods and compositions described herein are those that exert a cytotoxic effect.

A "cytotoxic agent" means an agent that has a cytotoxic effect on a cell, thereby depleting or inhibiting the growth of, respectively, cells within a cell population.

The term "deplete," in the context of the effect of a CD30 antibody on CD30-expressing cells, refers to a reduction in the number of, or elimination of, the CD30-expressing cells.

The terms "treatment" or "treat" refer to slowing, stopping, or reversing the progression of a CD30-expressing cancer in a patient, as evidenced by a decrease or elimination of a clinical or diagnostic symptom of the disease, by administration of a CD30-targeted therapy (e.g., an anti-CD30 antibody or antibody drug conjugate) to the subject after the onset of the clinical or diagnostic symptom of the CD30-expressing cancer at any clinical stage. Treatment can include, for example, a decrease in the severity of a symptom, the number of symptoms, or frequency of relapse.

The term "triple negative breast cancer" refers to breast cancer that clinically tests negative for estrogen receptors, progesterone receptors and HER2/neu protein.

The term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which a CD30 antibody is administered.

The term "effective amount," in the context of the administration of a pharmaceutical agent refers to the amount of the agent that is sufficient to inhibit the occurrence or ameliorate one or more clinical or diagnostic symptoms of a CD30-expressing cancer in a patient. An effective amount of an agent is administered according to the methods described herein in an "effective regimen." The term "effective regimen" refers to a combination of amount of the agent and dosage frequency adequate to accomplish treatment of a CD30-expressing cancer.

The term "patient" includes human and other mammalian subjects that receive diagnostic, prophylactic or therapeutic treatment.

Therapeutic agents are typically substantially pure from undesired contaminants. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% purity w/w can be obtained.

DETAILED DESCRIPTION

I. General

The invention provides, inter alia, methods of diagnosis, prognosis, prophylaxis and treatment and monitoring treatment of ovarian cancer (e.g., ovarian serous carcinoma), skin cancer (e.g., melanoma or skin squamous cell carcinoma), breast cancer (e.g., triple negative breast cancer), thyroid carcinoma (e.g., anaplastic thyroid carcinoma), pancreatic carcinoma (e.g., adenocarcinoma or undifferentiated pancreatic carcinoma), lung cancer (e.g., small cell or squamous cell), anal cancer (e.g., anal squamous cell carcinoma), thymic carcinoma, endometrial carcinoma, and carcinoma of unknown primary. The invention provides, inter alia, methods of diagnosis, prognosis, prophylaxis and treatment and monitoring treatment of genitourinary squamous cell carcinomas, gynecologic carcinosarcomas, urethral squamous cell carcinoma, uterine carcinosarcoma, sertoli cell tumor, leydig cell tumor, and pancreatic adenocarcinoma. In some aspects, antibodies to CD30 are used in the methods of diagnosis, prognosis, prophylaxis and treatment and monitoring treatment. The methods are premised in part on the results presented in the Examples showing that CD30 is expressed in certain cancers. The expression was detected in formalin fixed paraffin embedded (FFPE) samples from cancerous tissues using antibodies that bind to CD30.

II. Antibodies to CD30

Antibodies to CD30 can be used for detection of CD30 in cancer (e.g., ovarian cancer, skin cancer, breast cancer, thyroid carcinoma, pancreatic carcinoma, lung cancer, anal cancer, thymic carcinoma, endometrial carcinoma, and carcinoma of unknown primary) and for treatment thereof. Dependent upon the antibody's properties, certain antibodies are preferred for detection while others may be preferred for treatment.

A. Antibodies to CD30 in General

Anti-CD30 antibodies include monoclonal, chimeric (e.g., having a human constant region and mouse variable region), humanized, veneered, or human antibodies; single chain antibodies, or the like. The immunoglobulin molecules can be of any type or class (e.g., IgG, IgE, IgM, IgD, IgA and IgY) or subclass (e.g., IgG1, IgG2, IgG3, IgG4, IgA1 and IgA2).

Anti-CD30 antibodies can be an antigen-binding antibody fragment such as, a Fab, a F(ab'), a F(ab')$_2$, a Fd chain, a single-chain Fv (scFv), a single-chain antibody, a disulfide-linked Fv (sdFv), a fragment comprising either a $V_L$ or $V_H$ domain, including nanobodies or fragments from camels, llamas or the like, or fragments produced by a Fab expression library, or a CD30-binding fragments of any of the above antibodies described supra. Antigen-binding antibody fragments, including single-chain antibodies, can comprise the variable region(s) alone or in combination with the entirety or a portion of the following: hinge region, CH1, CH2, CH3 and CL domains. Also, antigen-binding fragments can comprise any combination of variable region(s) with a hinge region, CII1, CH2, CH3 and CL domains.

The antibodies can be mono-specific, bi-specific, tri-specific, or of greater multi-specificity. Multi-specific antibodies maybe specific for different epitopes of CD30 or may be specific for both CD30 as well as for a heterologous protein. (See, e.g., WO 93/17715; WO 92/08802; WO 91/00360; WO 92/05793; Tutt et al., 1991, J. Immunol. 147:60-69; U.S. Pat. Nos. 4,474,893; 4,714,681; 4,925,648; 5,573,920; and 5,601,819; Kostelny et al., 1992, J. Immunol. 148:1547-1553.) Multi-specific antibodies, including bi-specific and tri-specific antibodies, useful for practicing the methods described herein are antibodies that immunospecifically bind to both CD30 and a second cell surface receptor or receptor complex, such as an immunoglobulin gene superfamily member, a TNF receptor superfamily member, an integrin, a cytokine receptor, a chemokine receptor, a soluble protein, a major histocompatibility protein, a lectin (C-type, S-type, or I-type), or a complement control protein.

Anti-CD30 antibodies can also be described in terms of their binding affinity to CD30, of $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

An anti-CD30 antibody can be a chimeric antibody. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. (See, e.g., Morrison, Science, 1985, 229:1202; Oi et al., 1986, BioTechniques 4:214; Gillies et al., 1989, J. Immunol. Methods 125:191-202; U.S. Pat. Nos. 5,807,715; 4,816,567; and 4,816,397.)

An anti-CD30 antibody can also be a humanized antibody including a veneered antibody. Humanized antibodies are antibody molecules that bind the desired antigen and have one or more complementarity determining regions (CDRs) from a non-human species, and framework and constant regions from a human immunoglobulin molecule. Often, framework residues in the human framework regions will be substituted with the corresponding residue from the CDR donor antibody to alter, or preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riecbmann et al., 1988, Nature 332:323.) Antibodies can be humanized using a variety of techniques known in the art such as CDR-grafting (EP 0 239 400; WO 91/09967; U.S. Pat. Nos. 5,225,539; 5,530,101; and 5,585,089), veneering or resurfacing (EP 0 592 106; EP 0 519 596; Padlan, Molecular Immunology, 1991, 28(4/5):489-498; Studnicka et al., 1994, Protein Engineering 7(6):805-814; Roguska et al., 1994, PNAS 91:969-973), and chain shuffling (U.S. Pat. No. 5,565,332) (all of these references are incorporated by reference herein).

An anti-CD30 antibody can also be a human antibody. Human antibodies can be made by a variety of methods known in the art such as phage display methods (see supra) using antibody libraries derived from human immunoglobulin sequences. See also, e.g., U.S. Pat. Nos. 4,444,887 and 4,716,111; WO 98/46645, WO 98/50433, WO 98/24893, WO 98/16654, WO 96/34096, WO 96/33735, and WO 91/10741. In addition, a human antibody recognizing a selected epitope can be generated using a technique referred to as "guided selection," in which a selected non-human monoclonal antibody, e.g., a mouse antibody, is used to guide the selection of a completely human antibody recognizing the same epitope (see, e.g., Jespers et al., 1994, Biotechnology 12:899-903). Human antibodies can also be produced using transgenic mice that express human immunoglobulin genes. Monoclonal antibodies directed against the antigen can be obtained from the immunized, transgenic mice using hybridoma technology. For an overview of the technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598, 877; and U.S. Pat. Nos. 5,413,923; 5,625,126; 5,633,425; 5,569,825; 5,661, 016; 5,545,806; 5,814,318; 5,885,793; 5,916,771; and 5,939,598.

Antibodies can be assayed for specific binding to CD30 by known methods, such as for example, competitive and non-competitive immunoassay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays. (See, e.g., Ausubel et al., eds., *Short Protocols in Molecular Biology* (John Wiley & Sons, Inc., New York, 4th ed. 1999); Harlow & Lane, *Using Antibodies: A Laboratory Manual* (Cold Spring Harbor Laboratory Press, Cold Spring Harbor, N.Y., 1999.)

Further, the binding affinity of an antibody to CD30 and the off-rate of an antibody CD30 interaction can be determined by competitive binding assays. One example of a competitive binding assay is a radioimmunoassay comprising the incubation of labeled CD30 (e.g., $^3H$ or $^{125}I$) with the antibody of interest in the presence of increasing amounts of unlabeled CD30, and the detection of the antibody bound to the labeled CD30. The affinity of the antibody for CD30 and the binding off-rates can then be determined from the data by Scatchard plot analysis. Competition with a second antibody can also be determined using radioimmunoassays. In this case, CD30 is incubated with the antibody of interest conjugated to a labeled compound (e.g., $^3H$ or $^{125}I$) in the presence of increasing amounts of an unlabeled second antibody. Alternatively, the binding affinity of an antibody to CD30 and the on- and off-rates of an antibody-CD30 interaction can be determined by surface plasmon resonance.

Antibodies can be made using antigen-containing fragments of the CD30 protein by standard procedures according to the type of antibody (see, e.g., Kohler, et al., *Nature,* 256:495, (1975); Harlow & Lane, *Antibodies, A Laboratory Manual* (C.S.H.P., NY, 1988); Queen et al., *Proc. Natl. Acad. Sci. USA* 86:10029-10033 (1989) and WO 90/07861; Dower et al., WO 91/17271 and McCafferty et al., WO 92/01047 (each of which is incorporated by reference for all purposes). As an example, monoclonal antibodies can be prepared using a wide variety of techniques including, e.g., the use of hybridoma, recombinant, and phage display technologies, or a combination thereof. Hybridoma techniques are generally discussed in, e.g., Harlow et al., supra, and Hammerling, et al., *In Monoclonal Antibodies and T-Cell Hybridomas*, pp. 563-681 (Elsevier, N.Y., 1981). Examples of phage display methods that can be used to make the anti-CD30 antibodies include, e.g., those disclosed in Briinnan et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, Gene 187:9-18; Burton et al., 1994, *Advances in Immunology* 57:191-280; PCT Application No. PCT/GB91/01 134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Techniques for generating antibody fragments that recognize specific epitopes are also generally known in the art. For example, Fab and $F(ab')_2$ fragments can be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the $C_H1$ domain of the heavy chain. Techniques to recombinantly produce Fab, Fab' and $F(ab')_2$ fragments can also be employed using, e.g., methods disclosed in WO 92/22324; Mullinax et al., 1992, BioTechniques 12(6):864-869; and Sawai et al., 1995, AJRI 34:26-34; and Better et al., 1988, Science 240:1041-1043 (the disclosures of which are incorporated by reference herein).

Examples of techniques that can be used to produce single-chain Fvs and antibodies include those described in U.S. Pat. Nos. 4,946,778 and 5,258,498; Huston et al., 1991, *Methods in Enzymology* 203:46-88; Shu et al., 1993, *Proc. Natl. Acad. Sci.* USA 90:7995-7999; and Skerra et al., 1988, *Science* 240:1038-1040.

Anti-CD30 antibodies that are useful in the present methods can also be produced by recombinant expression techniques. Recombinant expression of an antibody that binds to CD30 and/or depletes or inhibits the proliferation of CD30-expressing cells requires construction of an expression vector containing a nucleic acid that encodes the antibody. Once a nucleic acid encoding such a protein has been obtained, the vector for the production of the protein molecule may be produced by recombinant DNA technology using techniques well known in the art. Standard techniques such as those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); Ausubel et al., *Short Protocols in Molecular Biology* (John Wiley & Sons, New York, 4th ed., 1999); and Glick & Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD30 antibody, an expression vector may encode a heavy or light chain thereof, or a heavy or light chain variable domain, operably linked to a promoter. An expression vector may include, e.g., the nucleotide sequence encoding the constant region of the antibody molecule (see, e.g., WO 86/05807; WO 89/01036; and U.S. Pat. No. 5,122,464), and the variable domain of the antibody may be cloned into such a vector for expression of the entire heavy or light chain. The expression vector is transferred to a host cell by known techniques, and the transfected cells are then cultured to produce the anti-CD30 antibody. Typically, for the expression of double-chained antibodies, vectors encoding both the heavy and light chains can be co-expressed in the host cell for expression of the entire immunoglobulin molecule.

A variety of prokaryotic and eukaryotic host-expression vector systems can be utilized to express an anti-CD30 antibody. Typically eukaryotic cells, particularly for whole recombinant anti-CD30 antibody molecules, are used for the expression of the recombinant protein. For example, mammalian cells such as Chinese hamster ovary cells (CHO) (e.g., DG44 or CHO-S) in conjunction with a vector such as the major intermediate early gene promoter element from human cytomegalovirus or the Chinese hamster ovary EF-1α promoter, is an effective expression system for the production of anti-CD30 antibodies (see, e.g., Foecking et al., 1986, Gene 45:101; Cockett et al., 1990, *Bio/Technology* 8:2; Allison, U.S. Pat. No. 5,888,809).

Other host-expression systems include, plasmid-based expression systems in bacterial cells (see, e.g., Ruther et al., 1983, *EMBO* 1,2:1791; Inouye & Inouye, 1985, *Nucleic Acids Res.* 13:3101-3109; Van Heeke & Schuster, 1989, *J. Biol. Chem.* 24:5503-5509); insect systems such as the use of *Autographa californica* nuclear polyhedrosis virus (AcNPV) expression vector in *Spodoptera frugiperda* cells; and viral-based expression systems in mammalian cells, such as, adenoviral-based systems (see, e.g., Logan & Shenk, 1984, *Proc. Natl. Acad. Sci. USA* 81:355-359; Bittner et al., 1987, *Methods in Enzymol.* 153:51-544).

B. Antibodies for Detection of CD30

Antibodies for detection of CD30 in the cancers described herein are those that specifically bind to CD30. Specific binding of a monoclonal antibody to its target antigen means an affinity of at least $10^6$, $10^7$, $10^8$, $10^9$, or $10^{10}$ $M^{-1}$ and is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Selection of antibodies to CD30 for use in detection methods depends on whether CD30 is detected by a technique that requires detection of denatured CD30 or native CD30 (as expressed on cells). Preferred antibodies for identification of patients that could benefit from CD30-directed therapy are those that specifically bind to an extracellular domain of CD30. In some aspects, the antibody will bind to CD30 on cancer specimens that are fixed with formalin and embedded in paraffin (FFPE), e.g., Ber-H2.

C. CD30-Directed Therapies

CD30-directed therapies include therapies with any cytotoxic agent that is directed to CD30. CD30-directed therapies include anti-CD30 antibodies and anti-CD30 antibody drug conjugates as well as other anti-CD30 binding agents and conjugates thereof.

Antibodies used for therapeutic applications specifically bind to an extracellular domain of native CD30 that is expressed on cancer cells. Although practice of the invention is not dependent on an understanding of mechanism, it is believed that the antibodies can exert a cytotoxic or cytostatic effect either as a result of binding to CD30 and being internalized within a cell, or by binding to CD30 and accumulating on the outside of cells. In either event, the cytotoxic effect can be promoted by conjugating the antibody to a cytotoxic agent. The cytotoxic effect exerted from the outside of the cell by an antibody bound to CD30 can additionally or alternatively be promoted by an antibody constant (effector) function. The antibody constant domains mediate various Ig effector functions, such as participation of the antibody in antibody dependent cellular cytotoxicity (ADCC), complement dependent cytotoxicity (CDC) and/or antibody dependent cellular phagocytosis (ADCP). Optionally, the effector function of a CD30-binding agent can be augmented by several approaches as described in US2012/0014943.

Anti-CD30 antibodies suitable for use in accordance with the present methods include any antibody that specifically binds to the CD30 antigen. Anti-CD30 antibodies of the present invention are preferably monoclonal and can include, for example, chimeric (e.g., having a human constant region and mouse variable region), humanized, or human antibodies. The immunoglobulin molecule is of the IgG type and can be any subclass (e.g., IgG1, IgG2, IgG3, IgG4) of immunoglobulin molecule and variants thereof. The immunoglobulin molecule is preferably an IgG1. Multispecific antibodies are suitable for use in accordance with the present methods as well. The antibodies of the present invention can be generated by any suitable method known in the art. Exemplary anti-CD30 antibodies include, but are not limited to, humanized or chimeric AC10 antibodies. Murine AC10 has been deposited under ATCC Accession Number PTA-6679. In an exemplary embodiment, the anti-CD30 antibody is the cAC10 antibody. As used herein, the cAC10 antibody is an antibody that has the heavy chain and light chain variable regions of murine AC10, a human gamma I constant region and a human kappa constant region.

Antibodies to CD30 can be conjugated to a cytotoxic or cytostatic moiety to form an antibody drug conjugate (ADC). Particularly suitable moieties for conjugation to antibodies are chemotherapeutic agents, prodrug converting enzymes, radioactive isotopes or compounds, or toxins. For example, an anti-CD30 antibody can be conjugated to a cytotoxic agent such as a chemotherapeutic agent, or a toxin (e.g., a cytostatic or cytocidal agent such as, e.g., abrin, ricin A, *pseudomonas* exotoxin, or diphtheria toxin). Examples of useful classes of cytotoxic agents include, for example, auristatins, camptothecins, duocarmycins, etoposides, maytansinoids, benzodiazepines (e.g., pyrrolo[1,4]benzodiazepines, indolinobenzodiazepines, and oxazolidinobenzodiazepines) and *vinca* alkaloids. Techniques for conjugating therapeutic agents to proteins, and in particular to antibodies, are well-known. (See, e.g., Alley et al., *Current Opinion in Chemical Biology* 2010 14:1-9; Senter, *Cancer J.,* 2008, 14(3):154-169.)

Suitable cytotoxic agents include, for example, auristatins (e.g., auristatin E, AFP, MMAF, MMAE), DNA minor groove binders (e.g., enediynes and lexitropsins), duocarmycins, taxanes (e.g., paclitaxel and docetaxel), *vinca* alkaloids, doxorubicin, morpholino-doxorubicin, and cyanomorpholino-doxorubicin.

Suitable antibody-drug conjugates include auristatin based antibody-drug conjugates meaning that the drug component is an auristatin drug. Auristatins bind tubulin, have been shown to interfere with microtubule dynamics and nuclear and cellular division, and have anticancer activity. The auristatin can be auristatin E or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include MMAF, and MMAE. The synthesis and structure of exemplary auristatins are described in U.S. Pat. Nos. 7,659,241, 7,498,298, 2009-0111756, 2009-0018086, and U.S. Pat. No. 7,968,687, each of which is incorporated herein by reference in its entirety and for all purposes.

Exemplary auristatin based antibody drug conjugates include vcMMAE, vcMMAF and mcMMAF antibody drug conjugates as shown below wherein Ab is an anti-CD30 antibody and val-cit represents the valine-citrulline dipeptide:

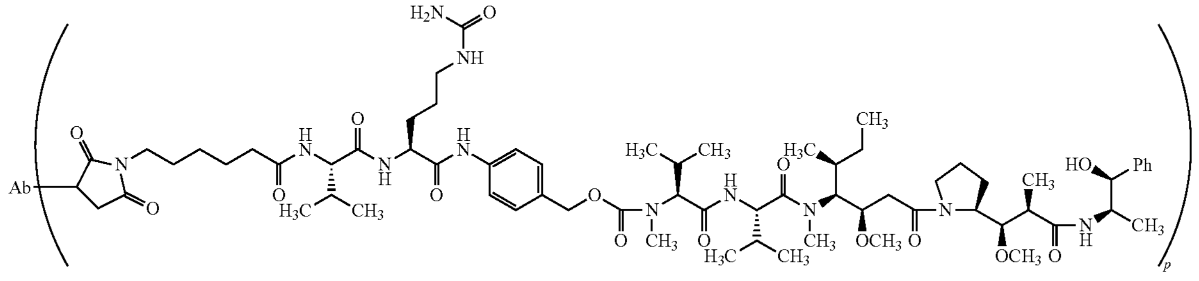

vcMMAE

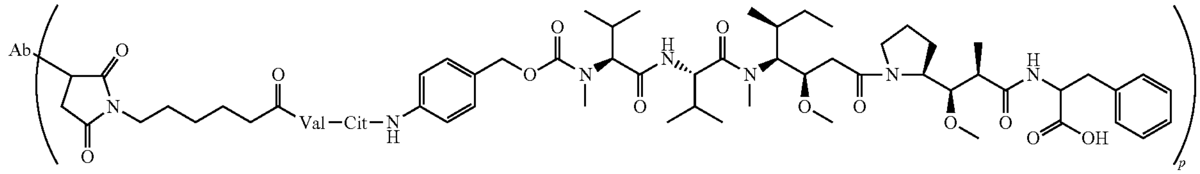

vcMMAF

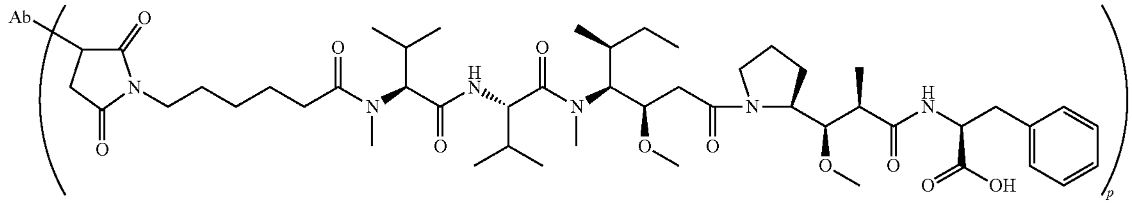

mcMMAF or a pharmaceutically acceptable salt thereof. The drug loading is represented by p, the number of drug-linker molecules per antibody. Depending on the context, p can represent the average number of drug-linker molecules per antibody, also referred to as the average drug loading. P ranges from 1 to 20 and is preferably from 1 to 8. In some preferred embodiments, when p represents the average drug loading, p ranges from about 2 to about 5. In some embodiments, p is about 2, about 3, about 4, or about 5. The average number of drugs per antibody in a preparation may be characterized by conventional means such as mass spectroscopy, HIC, ELISA, and HPLC.

In a particularly preferred embodiment, the anti-CD30 auristatin-based antibody drug conjugate is brentuximab vedotin, an antibody-drug conjugate which has the structure:

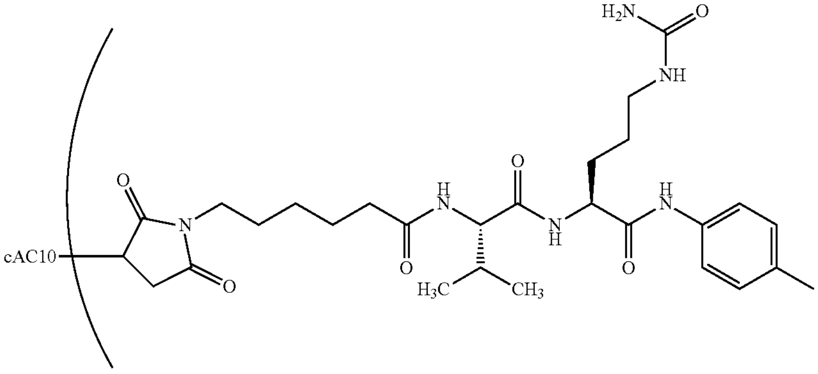

-continued

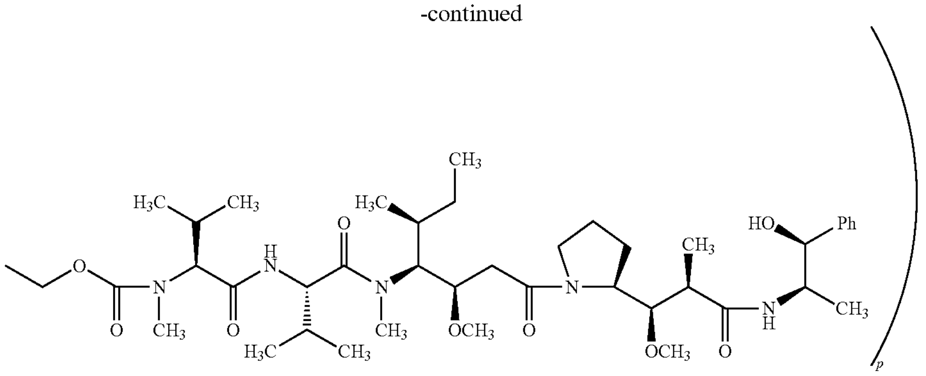

Brentuximab vedotin is a CD30-directed antibody-drug conjugate consisting of three components: (i) the chimeric IgG1 antibody cAC10, specific for human CD30, (ii) the microtubule disrupting agent MMAE, and (iii) a protease-cleavable linker that covalently attaches MMAE to cAC10. The drug to antibody ratio or drug loading is represented by "p" in the structure of Brentuximab Vedotin and ranges in integer values from 1 to about 8. The average drug loading in a pharmaceutical preparation is 3 to about 5.

III. Detecting CD30

The tissue samples to be assayed for diagnostic applications can be obtained by surgical procedures, e.g., biopsy. CD30 is typically detected by an immuno assay in which a sample containing cells known or suspected to be from a cancer ((e.g., ovarian (e.g., ovarian serous carcinoma), skin (e.g., melanoma and skin squamous cell carcinoma), breast (e.g., triple negative breast cancer), thyroid (e.g., anaplastic thyroid carcinoma), pancreatic (e.g., adenocarcinoma or undifferentiated pancreatic carcinoma), lung (e.g., small cell and squamous cell), anal (e.g., anal squamous cell carcinoma), thymic, endometrial) is contacted with an anti-CD30 antibody. After contact, the presence or absence of a binding event of the antibody to the cells in the sample is determined. The binding is related to the presence or absence of the antigen expressed on cancerous cells in this sample. In some aspects, after incubation with the anti-CD30 antibody, the sample is contacted with a labeled specific binding partner of the anti-CD30 antibody capable of producing a detectable signal. In other aspects, the anti-CD30 antibody itself can be labeled. Examples of types of labels include enzyme labels, polymer labels, radioisotopic labels, nonradioactive labels, fluorescent labels, toxin labels and chemoluminescent labels. Detection of a signal from the label indicates the presence of the antibody specifically bound to CD30 in the sample.

The tissue sample from the patient can be frozen, fresh, fixed, centrifuged, and/or embedded, e.g., paraffin embedded. Preferably, the sample on which the assay is performed is fixed or frozen to permit histological sectioning. Preferably, the excised tissue samples are fixed in aldehyde fixatives such as formaldehyde, paraformaldehyde, glutaraldehyde; or heavy metal fixatives such as mercuric chloride. More preferably, the excised tissue samples are fixed in formalin and embedded in paraffin wax prior to incubation with the antibody. An advantage afforded by formalin-fixed paraffin-embedded (FFPE) specimens is the preservation of cellular and architectural morphologic detail in tissue sections (see, e.g., Fox et al., 1985, *J. Histochem. Cytochem.* 33:845-853). Optionally, FFPE specimens can be treated with Tris-EDTA high pII or citrate and heat to increase accessibility of epitopes (see, e.g., Shi et al., 1991, *J Histochem Cytochem.* 39:741-748).

In some embodiments, immunohistochemistry techniques are used to detect CD30. Immunohistochemistry refers to the process of detecting antigens in cells of a tissue section based on the principle of specific antibody and antigen interactions. Bound antibodies can be detected in a number of ways, including, for example, fluorescent detection methods, enzymatic detection methods, and polymer based detection systems.

Alternatively, a protein fraction can be isolated from cells from known or suspected cancer and analyzed by ELISA, Western blotting, immunoprecipitation or the like. In another variation, cells can be analyzed for expression of CD30 by flow cytometry analysis, preferably in combination with other cancer cell markers.

Detection of CD30 can be by methods other than those that utilize antibodies. For example, mRNA can be extracted from cells from known or suspected to be cancer. The mRNA or a nucleic acid derived therefrom, such as a cDNA can then be analyzed by hybridization to a nucleic probe binding to DNA encoding CD30. Alternatively, RT-PCR can be performed.

In another variation, a cancer (e.g., ovarian, pancreatic, skin, breast, thyroid, pancreatic, small cell lung, anal, thymic, or endometrial cancer or carcinoma of unknown primary) can be detected in vivo by administering a labeled anti-CD30 antibody to a patient and detecting the antibody by in vivo imaging.

Detection of CD30 in tissue samples can be qualitative or quantitative or both. Qualitative detection means detecting the presence or absence of CD30 expression. Quantitative expression means determining a level of expression of expression of CD30. The presence and/or level of CD30 in cancer tissue sample at issue can (but need not) be determined with respect to one or more standards. The standards can be historically or contemporaneously determined. The standard can be, for example, a sample known not to be cancerous from a different subject, a tissue from either the patient or other subject known not to express CD30, or a corresponding cell line. The standard can also be the patient sample under analysis contacted with a control antibody that does not bind to CD30. Because CD30 is not expressed to any significant extent in non-cancerous ovarian, pancreatic, skin, breast, endometrial, thyroid, pancreatic, small cell lung, anal, or thymic tissue, such non-cancerous tissue can be used as a zero (background) expression standard when tested with a specific CD30 detection method.

The presence of detectable signal from binding of an anti-CD30 antibody to CD30 relative to a standard (if used) indicates the presence of CD30 in the tissue sample, and the level of detectable binding provides an indication of the level of expression of CD30. The level of expression can be expressed as a percentage of malignant or atypical cells in a sample showing detectable expression of CD30. For example, in assays performed on tissue sections, the level of expression can be expressed as a percentage of malignant or atypical cells in the tissue section showing detectable expression of CD30. Alternatively, or additionally, the level (intensity) of expression can be used as a measure of the total expression in the sample or of the cells expressing CD30 in the sample.

In some aspects, the presence of detectable signal from binding of an anti-CD30 antibody is sufficient to identify a patient for treatment with a CD30-directed therapy. In some aspects, a level of expression of at least 10% is used to identify a patient for treatment with CD30-directed therapy (e.g., therapy with an anti-CD30 antibody or anti-CD30 antibody drug conjugate) wherein the level of expression is a percentage of the malignant and/or atypical cells in a sample (e.g., a tissue section) showing detectable expression of CD30. In some aspects, a level of expression of at least 15% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 20% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 25% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 30% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 35% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 40% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 45% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 50% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 75% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 80% is used to identify a patient for treatment with CD30-directed therapy wherein the level of expression is a percentage of the malignant and/or atypical cells in a sample (e.g., tissue section) showing detectable expression of CD30. In some aspects, a level of expression of at least 85% is used to identify a patient for treatment with CD30-directed therapy wherein the level of expression is a percentage of the malignant and/or atypical cells in a sample (e.g., tissue section) showing detectable expression of CD30. In any of these embodiments, the intensity of expression can be determined as well and used to obtain a measure of the total expression in the sample or of the cells expressing CD30 in the sample.

In some aspects, CD30 expression is detected in the cell membrane, Golgi, and/or cytoplasm.

IV. Diagnosis, Prognosis, Designing and Monitoring Treatment

Detection of expression of CD30 in a tumor sample from a patient with cancer (e.g., ovarian, pancreatic, skin, breast, thyroid, pancreatic, genitourinary, gynecologic, lung, anal, urethral, uterine, thymic, or endometrial cancer or carcinoma of unknown primary cancer) can be an indication that the sample is cancerous. The indication of cancer provided by presence and/or level of CD30 can be combined with means of diagnosis, such as internal or external examination of a patient by a physician, X-ray, CT Scan (Computed Tomography), PET Scan (Positron Emission Tomography), PET/CT Scan, ultrasound, MRI (Magnetic Resonance Imaging), endoscopy, ERCP (Endoscopic Retrograde Cholangiopancreatography), histological examination, cytogenetics, and tissue culturing in arriving at an overall diagnosis.

Perhaps of greatest relevance to the physician, the presence and level of CD30 provides useful information for designing a treatment protocol for the patient, and in particular administering a CD30-directed therapy. Because of the essential absence of detectable CD30 expression in normal tissue, the presence of this receptor in a cancer provides a target for therapeutic treatment. Continued analysis of CD30 after treatment provides a means of monitoring whether the treatment is effective, a reduction in the level of CD30-positive signal (i.e., as a proxy for the presence of CD30-positive cancer cells) that the treatment is effective.

V. Patients Amenable to Treatment

Patients amenable to treatment by the methods usually have detectable levels of CD30 in their cancerous tissue accompanied by other signs or symptoms of cancer as described above. In some embodiments, patients amenable to treatment by the present methods only need have detectable levels of CD30 in their cancerous tissue. In other embodiments, patients amenable to treatment by the present method have a level of CD30 expression of at least 10%, at least 15%, at least 20%, at least 25%, at least 30%, at least 35%, at least 40%, at least 45%, at least 50%, at least 60%, at least 70%, at least 75%, at least 80%, or at least 85% wherein the level of expression is a percentage of the malignant and/or atypical cells in a sample showing detectable expression of CD30. In preferred embodiments, at least 10%, 15%, 20%, 25%, 30%, 35%, 40%, 45%, 50%, 60%, 70%, 75%, 80%, or 85% of the cells in the sample express CD30 when using an anti-CD30 antibody specific for CD30

(e.g., the BerH2 antibody) as the detection antibody. The sample is typically a tumor sample taken from the patient.

Sometimes, patients treated by the present methods have undergone other types of treatment previously (e.g., surgery, chemotherapy and/or radiation) without inducing remission or even slowing down the growth of the cancer. In some such patients, the cancer is refractory to treatment by one of more such therapies.

Sometimes, patients treated by the present methods have undergone other types of treatment previously (e.g., surgery, chemotherapy and/or radiation) but have relapsed.

Sometimes, patients treated by the present methods are treatment naïve (e.g., have not undergone surgery, chemotherapy or radiation for their cancer). Sometimes, patients treated by the present methods are newly diagnosed.

Some patients at risk of cancer can also be treated prophylactically before signs and symptoms of the disease appear. Such individuals include those having relatives who have experienced these diseases, and those whose risk is determined by analysis of genetic or biochemical markers.

VI. Methods of Treatment

The present invention provides methods of treating or prophylaxis of CD30-expresssing cancer (e.g., ovarian cancer, skin cancer, breast cancer, thyroid carcinoma, pancreatic carcinoma, lung cancer, squamous cell lung cancer, anal cancer, uterine cancer, urethral cancer, endometrial cancer, carcinoma of unknown primary, thymic carcinoma, genitourinary squamous cell carcinomas, gynecologic carcinosarcomas, sertoli cell tumors, leydig cell tumors, and pancreatic adenocarcinoma) by CD30-directed therapy (e.g., the antibodies, and ADC, and other anti-CD30 binding agents (collectively agents) disclosed herein). The compositions can be administered to a patient. In some aspects, the ovarian cancer is ovarian serous carcinoma; the skin cancer is melanoma or skin squamous cell carcinoma; the breast cancer is triple negative breast cancer; the lung cancer is small cell lung cancer or squamous cell lung cancer, the thyroid carcinoma is anaplastic thyroid carcinoma; the pancreatic carcinoma is adenocarcinoma or undifferentiated pancreatic carcinoma; and the anal cancer is anal squamous cell carcinoma.

Various delivery systems can be used to administer the agents including intradermal, intramuscular, intraperitoneal, intravenous, subcutaneous, intranasal, epidural, and oral routes. The agents can be administered, for example by infusion or bolus injection, by absorption through epithelial or mucocutaneous linings (e.g., oral mucosa, rectal and intestinal mucosa, and the like) and can be administered together with other biologically active agents such as chemotherapeutic agents. Administration can be systemic or local.

The agents can be administered by injection, by means of a catheter, by means of a suppository, or by means of an implant, the implant being of a porous, non-porous, or gelatinous material, including a membrane, such as a sialastic membrane, or a fiber.

Alternatively, the agents can be delivered in a controlled release system. For example, a pump can be used (see Langer, 1990, *Science* 249:1527-1533; Sefton, 1989, *CRC Crit. Ref Biomed. Eng.* 14:201; Buchwald et al., 1980, *Surgery* 88:507; Saudek et al., 1989, *N. Engl. J. Med.* 321:574). Alternatively, polymeric materials can be used (see *Medical Applications of Controlled Release* (Langer & Wise eds., CRC Press, Boca Raton, Florida, 1974); *Controlled Drug Bioavailability, Drug Product Design and Performance* (Smolen & Ball eds., Wiley, New York, 1984); Ranger & Peppas, 1983, *Macromol. Sci. Rev. Macromol. Chem.* 23:61. See also Levy et al., 1985, *Science* 228:190; During et al., 1989, *Ann. Neurol.* 25:351; Howard et al., 1989, *J. Neurosurg.* 71:105.) Other controlled release systems are discussed, for example, in Langer, supra.

The agents can be administered as pharmaceutical compositions comprising a therapeutically or prophylactically effective amount of the agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, pH buffering agents (e.g., amino acids) and/or solubilizing or stabilizing agents (e.g., nonionic surfactants such as tween or sugars such as sucrose, trehalose or the like). These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein, typically in purified form, together with a suitable amount of carrier so as to provide the form for proper administration to the patient. The formulations correspond to the mode of administration.

Typically, compositions for intravenous administration are solutions in sterile isotonic aqueous buffer. When necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or a concentrate in a hermetically sealed container such as an ampoule or sachette indicating the quantity of active agent. When the pharmaceutical is to be administered by infusion, it can be dispensed with an infusion bottle containing sterile pharmaceutical grade water or saline. When the pharmaceutical is administered by injection, an ampoule of sterile water for injection or saline can be provided so that the ingredients can be mixed prior to administration.

The amount of the agent that is effective in the treatment or prophylaxis of the cancer can be determined by standard clinical techniques. In addition, in vitro assays may optionally be employed to help identify optimal dosage ranges. The precise dose to be employed in the formulation also depends on the route of administration, and the stage of the cancer, and should be decided according to the judgment of the practitioner and each patient's circumstances. Effective doses may be extrapolated from dose-response curves derived from in vitro or animal model test systems. A dose can be formulated in animal models to achieve a circulating plasma concentration range that includes the $IC_{50}$ (i.e., the concentration of the test compound that achieves a half-maximal inhibition of symptoms) as determined in cell culture.

For example, toxicity and therapeutic efficacy of the agents can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibit large therapeutic indices are preferred. When an agent exhibits toxic side effects, a delivery system that targets the agent to the site of affected tissue can be used to minimize potential damage to non-CD30-expressing cells and, thereby, reduce side effects.

Generally, the dosage of an antibody or ADC administered to a patient with a CD30-expressing cancer is 0.01 mg/kg to 25 mg/kg of the subject's body weight or 0.1 mg/kg to 25 mg/kg of the subject's body weight. More typically, the dosage administered to a subject is 0.1 mg/kg to 10 mg/kg of the subject's body weight, even more typically 0.1 mg/kg to 5 mg/kg, 0.1 mg/kg to 3 mg/kg of the subject's body weight. Generally, human antibodies have a longer half-life within the human body than antibodies from other species due to the immune response to the foreign proteins. Thus, lower dosages of ADCs comprising humanized, chimeric or human antibodies and less frequent administration is often possible.

The recommended dose for brentuximab vedotin for the treatment of Hodgkin Lymphoma or Anaplastic Large Cell Lymphoma is 1.8 mg/kg administered every three weeks until a maximum of 16 cycles. Although the current recommended dose is 1.8 mg/kg for Hodgkin Lymphoma, other higher or lower doses are contemplated for other cancers including, for example, 2.4 mg/kg. Administration is by intravenous infusion over 30 minutes. In an exemplary embodiment, brentuximab vedotin will be provided for the patients described herein at a dose of 1.8 mg/kg or 2.4 mg/kg administered every three weeks. Other dosing regimens and routes of administration, however, are contemplated and encompassed by the present invention. One exemplary alternative dosing regimen is weekly dosing every 3 out of 4 weeks at about 0.8 mg/kg to about 1.2 mg/kg. The frequency of administration and dosage amount depends upon many factors including the condition of the patient and severity of disease.

CD30-directed therapy can also be administered in combination (including sequentially) with one or more other therapeutic agents for the treatment of cancer, in particular, CD30-directed therapy can be administered with other therapies that are standard of care (e.g., front-line standard of care or second or third line treatment or even salvage therapy) for the particular disease to be treated. In some aspects, combination therapy can include a second cytostatic or cytotoxic agent (for example, an unconjugated cytostatic or cytotoxic agent such as those conventionally used for the treatment of cancers). Combination therapy can also include, e.g., administration of an agent that targets a receptor or receptor complex other than CD30 on the surface of CD30-expressing cancer cells. Typically, such an antibody or ligand binds to a cell surface receptor on CD30-expressing cancer cells or other cells within the tumor and enhances the cytotoxic effect of the anti-CD30 antibody by delivering a cytotoxic signal to the CD30-expressing cancer cells or by reducing anti-apoptosis mechanisms.

Other drugs that can administered with the agent include growth factor inhibitors, or anti-angiogenesis factors. The present methods can be combined with other means of treatment such as surgery, radiation, targeted therapy, immunotherapy, use of growth factor inhibitors, or anti-angiogenesis factors.

Surgery is a preferred treatment and is frequently necessary to obtain a tissue specimen for differential diagnosis via its histology. Improved survival is attributed to more accurate staging of the disease and a higher rate of aggressive surgical excision of tumor. The type of surgery depends upon how widespread the cancer is when diagnosed (the cancer stage), as well as the presumed type and grade of cancer.

CD30-directed therapy can be administered concurrently to a patient undergoing surgery, chemotherapy or radiation therapy treatments. In some other embodiments, a patient can undergo surgery, chemotherapy or radiation therapy prior or subsequent to administration of a CD30-directed therapy by at least an hour and up to several months, for example at least an hour, five hours, 12 hours, a day, a week, a month, or three months, prior or subsequent to administration of the ADC.

The invention is further described in the following examples, which are not intended to limit the scope of the invention.

EXAMPLES

CD30 Expression in Tumor and Non-Tumor Cancerous Tissue Using Ber-H2 Antibody Tumor tissues were obtained from patients with ovarian cancer (e.g., ovarian serous carcinoma), skin cancer (e.g., melanoma, and skin squamous cell carcinoma), breast cancer (e.g., triple negative breast cancer), thyroid carcinoma (e.g., anaplastic thyroid carcinoma), pancreatic carcinoma (e.g., undifferentiated pancreatic carcinoma or adenocarcinoma), lung cancer (e.g., small cell and squamous cell), anal cancer (e.g., anal squamous cell carcinoma), endometrial cancer, carcinoma of unknown primary, thymic carcinoma, genitourinary squamous cell carcinoma, gynecologic carcinosarcoma, Leydig cell tumor, and Sertoli cell tumor. The tissue samples were fixed and embedded into paraffin according to routine procedures. Tissue sections (4-6 microns) were prepared from paraffin blocks.

An indirect IHC technique assay was used to detect CD30 using an anti-CD30 antibody (commercially available clone Ber-H2). In this method, an unconjugated primary antibody (Ber-H2 at 2 ug/ml) was used as the primary antibody. Endogenous peroxidase activity was neutralized using a peroxidase-blocking step. The EnVision™ FLEX+polymer based system (Dako, Glostrup, Denmark) was used for CD30 detection. The polymer technology uses an enzyme labeled molecule of dextran to which an average of 70 molecules of enzyme and 10 molecules of secondary antibodies are attached. Substrate chromogen (either 3,3-diaminobenzidine (DAB) or a red detection system) was added and a brown or red (respectively) precipitate attached to the labeled polymer. The slides were then counterstained with hematoxylin to complete the staining procedure. The slides were evaluated by a pathologist. The CD30 signal was detected as membrane, cytoplasmic, Golgi, or combinations of the three subcellular localizations. Negative controls and appropriate positive controls were used for each staining run. The immunohistochemical (IHC) expression of CD30 was evaluated based on percentage of tumor involved. The results of all the tumor tissues are shown on Table 1.

| Tumor type | Number of $CD30^+$ cases | Percentage of tumor cells that express CD30 in $CD30^+$ cases |
|---|---|---|
| Ovarian carcinoma | 19/293 | 10% to 80% |
| Melanoma | 7/121 | 10% to 50% |
| Triple negative breast cancer | 4/106 | 15% to 80% |
| Anaplastic thyroid carcinoma | 1/1 | 12% |
| Pancreatic carcinoma | 2/105 | 45% to 60% |
| Small cell lung cancer | 1/105 | 50% |
| Squamous cell carcinoma of the lung | 1/63 | 30% |
| Skin squamous cell carcinoma | 1/9 | 15% |
| Anal squamous cell carcinoma | 1/12 | 80% |
| Endometrial carcinoma | 1/61 | 15% |
| Carcinoma of unknown primary | 1/37 | 30% |
| Genitourinary squamous cell carcinoma | 1/2 | 10% |
| Gynecologic carcinosarcoma | 1/10 | 15% |
| Leydig cell tumor | 1/2 | 100% |
| Sertoli cell tumor | 1/1 | 98% |

Treatment of $CD30^+$ patients

Patents with $CD30^+$ ovarian cancer, breast cancer, pancreatic cancer, and melanoma were treated with brentuximab vedotin administered IV every 3 weeks at 1.8 mg/kg. Twelve patients with ovarian cancer were treated and five achieved stable disease. Two patients with breast cancer were treated and one patient achieved stable disease. One patient with melanoma was treated and achieved stable disease. One patient with pancreatic cancer was treated and achieved a partial response at cycle 12.

The present invention is not limited in scope by the specific embodiments described herein. Various modifications of the invention in addition to those described herein will become apparent to those skilled in the art from the foregoing description and accompanying figures. Such modifications are intended to fall within the scope of the appended claims. Unless otherwise apparent from the context any step, element, embodiment, feature or aspect of the invention can be used in combination with any other. All patent filings, and scientific publications, accession numbers and the like referred to in this application are hereby incorporated by reference in their entirety for all purposes to the same extent as if so individually denoted.

What is claimed is:

1. A method of treating a CD30 positive melanoma, comprising administering an effective regimen of brentuximab vedotin to a patient having the melanoma, wherein at least 10% of the malignant or atypical cells in a sample of the melanoma have been identified as expressing CD30.

2. The method of claim 1, wherein at least 50% of the malignant or atypical cells in the sample have been identified as expressing CD30.

3. The method of claim 1, wherein CD30 expression is detected in the cell membrane and/or Golgi of the malignant or atypical cells.

4. The method of claim 3, wherein CD30 expression is detected after fixing the malignant or atypical cells with formalin and embedding in paraffin.

* * * * *